United States Patent [19]

Thompson

[11] Patent Number: 5,482,932
[45] Date of Patent: Jan. 9, 1996

[54] ALGINATE GELS TO THE FORM OF FIBROUS PASTES USEFUL AS WOUND DRESSINGS

[75] Inventor: Joseph Thompson, Coventry, United Kingdom

[73] Assignee: Courtaulds Fibres (Holdings) Limited, London, United Kingdom

[21] Appl. No.: 116,791

[22] Filed: Sep. 7, 1993

[30] Foreign Application Priority Data

Sep. 4, 1992 [GB] United Kingdom ............... 9218749

[51] Int. Cl.$^6$ ............... A61K 31/715; A61K 9/70; A61L 15/00; C08B 37/04
[52] U.S. Cl. ............... 514/54; 424/443; 424/445; 424/447; 514/944; 514/953; 536/3; 536/123.1
[58] Field of Search ............... 536/3, 123.1; 514/54; 424/443, 445, 447

[56] References Cited

U.S. PATENT DOCUMENTS

| | | | |
|---|---|---|---|
| 2,477,861 | 8/1949 | Clark et al. | 260/209.6 |
| 3,611,732 | 10/1971 | Epstein | 61/36 |
| 3,640,741 | 2/1972 | Etes | 106/170 |
| 3,664,781 | 5/1972 | Widman | 425/68 |
| 3,865,765 | 2/1975 | Drelich et al. | 524/28 |
| 4,066,796 | 1/1978 | McKee | 426/302 |
| 4,117,172 | 9/1978 | Bradshaw et al. | 426/176 |
| 4,296,140 | 10/1981 | Jacquith et al. | 426/575 |
| 4,335,067 | 6/1982 | Castanis et al. | 264/222 |
| 4,393,048 | 7/1983 | Mason et al. | 424/132 |
| 4,713,084 | 12/1987 | Bohrn et al. | 8/561 |
| 5,089,606 | 2/1992 | Cole et al. | 536/54 |
| 5,139,783 | 8/1992 | Handjani et al. | 424/401 |
| 5,238,685 | 8/1993 | Wren | 424/445 |
| 5,302,399 | 4/1994 | Otagiri et al. | 424/493 |

FOREIGN PATENT DOCUMENTS

| | | |
|---|---|---|
| 048123 | 3/1982 | European Pat. Off. . |
| 048556 | 3/1982 | European Pat. Off. . |
| 070023 | 1/1983 | European Pat. Off. . |
| 085919 | 8/1983 | European Pat. Off. . |
| 0146904 | 7/1985 | European Pat. Off. . |
| 0380254 | 8/1990 | European Pat. Off. . |
| 0459733 | 12/1991 | European Pat. Off. . |
| 0459378 | 12/1991 | European Pat. Off. . |
| 2663229 | 12/1991 | France . |
| 3228231 | 2/1984 | Germany . |
| 3511721 | 10/1986 | Germany . |
| 49-000393 | 1/1974 | Japan . |
| 49-122558 | 11/1974 | Japan . |
| 49-048591 | 12/1974 | Japan . |
| 50-089685 | 7/1975 | Japan . |
| 51-136984 | 11/1976 | Japan . |
| 52-011224 | 1/1977 | Japan . |
| 52-053898 | 4/1977 | Japan . |
| 53-125311 | 11/1978 | Japan . |
| 54-151115 | 11/1979 | Japan . |
| 56-049153 | 5/1981 | Japan . |
| 57-002822 | 1/1982 | Japan . |
| 58-040051 | 3/1983 | Japan . |
| 59-074984 | 4/1984 | Japan . |
| 60-099336 | 6/1985 | Japan . |
| 62-074933 | 4/1987 | Japan . |
| 63-109779 | 5/1988 | Japan . |
| 63-301201 | 12/1988 | Japan . |
| 01045401 | 2/1989 | Japan . |
| 3083585 | 4/1991 | Japan . |
| 3195489 | 8/1991 | Japan . |
| 03266946 | 11/1991 | Japan . |
| 363622 | 1/1974 | Sweden . |
| 1171474 | 8/1985 | U.S.S.R. . |
| 662081 | 11/1951 | United Kingdom . |
| 760030 | 10/1956 | United Kingdom . |
| 0882565 | 11/1961 | United Kingdom . |
| 1073772 | 1/1968 | United Kingdom . |
| 1197785 | 7/1970 | United Kingdom . |
| 1375572 | 11/1974 | United Kingdom . |
| 1394741 | 5/1975 | United Kingdom . |
| 2013708 | 8/1979 | United Kingdom . |
| 1587930 | 4/1981 | United Kingdom . |
| 2098236 | 11/1982 | United Kingdom . |
| 2114417 | 8/1983 | United Kingdom . |
| 2222081 | 2/1990 | United Kingdom . |
| WO84/03705 | 9/1984 | WIPO . |
| WO87/04350 | 7/1987 | WIPO . |
| WO89/12471 | 12/1989 | WIPO . |

OTHER PUBLICATIONS

G. Blaine, "Experimental observations on absorbable alginate products in surgery (gel, film, gauge and foam)", *Annals of Surgery*, 125(1):102–114 (Jan. 1947).
R. H. McDowell, "Alginate gels", *Properties of Alginates*, 5th Edition, pp. 31–35 (1986).
A. Rosevear, "Immobilised biocatalysts—a critical review", *J. Chem. Tech. Biotechnol.*, 34B:133–134 (Jun., 1984).
M. Yonese et al, "Gelling process of alginate gel spheres having various counterions and their equilibrium swellings", *Nippon Kagaku Kaishi*, 2:198–202 (1992) [abstract only].
A. Begin et al, "Production of alginate beads by a rotative atomizer", *Biotechnol. Tech.*, 5(6):459–464 (Jun., 1991) [abstract only].
J. C. Ogbonna et al, "Production of micro–gel beads by a rotating disk atomizer", *J. Ferment. Bioeng.*, 68(1):40–48 (Jan., 1989) [abstract only].
S. C. Nigam et al, "Techniques for preparing hydrogel membrane capsules", *Biotechnol. Tech.*, 2(4):271–276 (Apr., 1991) [abstract only].
I. A. Velicky et al, "The production of ethanol by *Saccharomyces cerevisiae* immobilized in polycation–stabilized calcium alginate gels", *Biotechnol. Lett.*, 3(6):275–280 (Jun., 1981) [abstract only].
Izyumov et al, "Manufacture of calcium alginate gels", Izv. Vyssh. Ucheb. Zaved. Pishch. Tekhnol., 1:40–42 (1973) [abstract only].

*Primary Examiner*—Douglas W. Robinson
*Assistant Examiner*—Howard C. Lee
*Attorney, Agent, or Firm*—Howson and Howson

[57] ABSTRACT

The invention provides alginate gels which have the form of a fibrous paste and which particularly have an alginate content (expressed as alginic acid) in the range 2 to 11 percent by weight. The gels may be prepared by treating a water-insoluble or water-swellable alginate fiber, for example calcium alginate fiber, with an aqueous solution of a solubilizing salt, for example sodium chloride. The new gels are easier to handle than known alginate gels and are useful in wound dressing applications.

12 Claims, No Drawings

ALGINATE GELS TO THE FORM OF FIBROUS PASTES USEFUL AS WOUND DRESSINGS

This invention relates to alginate gels and their manufacture, particularly for use as wound dressings and in other medical and surgical applications.

Alginates are naturally occurring substances which are extracted from brown seaweed. They are polysaccharides which are copolymers of guluronic acid (G) and mannuronic acid (M). The proportions of G and M in the polymer, and the distribution of G and M blocks in the polymer, depends on the source of the alginate. Some alginates, for example sodium and potassium alginates, are soluble in water. Other alginates, for example calcium and zinc alginates, are insoluble in water, as is alginic acid. Water-insoluble alginate fibres have been made by extrusion of an aqueous solution of a water-soluble alginate, for example sodium alginate, through a spinnerette into an aqueous solution containing a precipitating (insolubilising) cation, for example calcium. Water-soluble alginate fibres have been made by extrusion of an aqueous solution of a water-soluble alginate, through a spinnerette into a precipitating bath of a hydrophilic organic solvent, for example ethanol. Alginate gels have been made by mixing an aqueous solution of a water-soluble alginate with an aqueous solution containing a precipitating cation.

The use of alginate materials in surgical dressings is well known, for example in the form of powders, fibers and gels. Alginate materials used in dressings may incorporate smaller or larger amounts of cations such as zinc, copper, silver, cerium, manganese or cobalt for therapeutic purposes. Alginate fibres may be used in dressings in the form of woven, knitted or non-woven fabrics. The alginate material used in dry alginate dressings (powders and fibers) is commonly calcium alginate or calcium sodium alginate in which the equivalent ratio of calcium to sodium is in the range 30:70 to 70:30 or 95:5. Dry alginate dressings may have a dehydrating effect on a wound, and it is common practice to wet such dressings with water or saline solution before application to the wound. Alginate gels used in wound dressing applications are commonly calcium sodium alginate gels. Such gels have a high moisture content and do not require wetting before application.

Alginate materials which contain both a solubilizing cation such as sodium and an insolubilizing cation such as calcium may be preferred in some wound dressing applications. Such materials have a higher hydrophilicity and are more absorbent than those containing an insolubilizing cation alone. Calcium sodium alginate fibers and gels are examples of such materials. Calcium sodium alginate fibers have good mechanical properties and are easy to handle, but their manufacture is a complex process involving partial replacement of the calcium ions in calcium alginate fiber by sodium ions. Known alginate gels are amorphous materials which are difficult to handle. It is an object of the invention to provide alginate gels with improved mechanical properties. It is another object of the invention to provide a convenient method of making such gels.

G. Blaine, in Annals of Surgery, Volume 125 (1947), pages 102–114, describes the reaction of an aqueous sodium alginate solution with aqueous calcium chloride solution to form an alginate gel in the form of a soft, pliable clot.

Alginates are reviewed in 'Properties of Alginates' by R. H. McDowell, 5th edition (1986), published by Kelco International (London). That publication states that alginate gel can be prepared by introduction of calcium ions into sodium alginate solution. High-strength gels are prepared from alginates containing a high proportion of G blocks. Reaction between free calcium ions and alginate is very rapid, so that the introduction of sufficient calcium to give strong irreversible gels poses the problem of its distribution throughout the whole volume without the shearing which would break down the rapidly formed gel network.

WO-A-89/12471 describes a wound dressing prepared by wetting a pad comprising mixed salt alginate fibers which have first and second cations, the first cation (for example calcium) being capable of forming an insoluble alginate salt and the second cation (for example sodium) being capable of forming a soluble alginate salt, the equivalent ratio of the first to second cations being from 30:70 to 70:30, and preferably about 50:50. Because of the properties of the second (solubilizing) cation, the sheet acquires gel-like qualities when wetted. The wetting liquid is preferably a sterile aqueous liquid such as distilled water or saline. The pad is generally provided in the form of a sheet, which may be a woven, knitted or preferably non-woven sheet.

The invention provides in one aspect an alginate gel, characterized in that it has the form of a fibrous paste which has an alginate content (expressed as alginic acid) in the range 2 to 11 percent by weight.

The invention provides in another aspect a method of making an alginate gel, characterized in that water-insoluble or water-swellable alginate fiber is treated with an aqueous solution of a solubilising salt so as to form the gel in the form of a fibrous paste. A solubilizing salt is defined as a salt which contains a cation which is capable of forming a water-soluble alginate salt, and this cation may be referred to as a solubilizing cation.

The alginate gel in the form of a fibrous paste according to the invention has the form of a viscous paste which is readily deformable, for example by molding, spreading or extrusion through an orifice. The alginate gel of the invention generally takes the form of a transparent or translucent hydrocolloid or hydrogel. Fibrous structure can be seen in the gel either with the naked eye or microscopically, and fibrous material can be manually drawn in small amounts from it. Alginate gels of the invention can be handled considerably more easily than prior art alginate gels and have good shape retention.

The alginate content of the fibrous gel according to the invention (expressed as alginic acid as beforesaid) is preferably no more than 10 per cent by weight. The alginate content of the gel may be at least 3 or 4 percent by weight. Gels having an alginate content in the range 3 to 7 per cent by weight may be preferred.

The fibrous alginate gel according to the invention preferably contains sodium as solubilizing cation and calcium as insolubilizing cation. These cations may be used alone or in conjunction with other suitable cations. The insolubilizing cation may comprise a polymeric cation, for example chitosan. The fibrous alginate gel according to the invention generally has a sodium ion content in the range 0.6 to 1.4% by weight, preferably in the range 0.6 to 1.0%, more preferably in the range 0.6 to 0.9%, further preferably in the range 0.65 to 0.75%, by weight. The fibrous gel of the invention may be isotonic or moderately hypotonic or hypertonic. The fibrous gel of the invention may alternatively be highly hypertonic, containing for example at least 5 per cent or at least 10 per cent by weight sodium chloride. The gel according to the invention preferably has a calcium ion content of no more than 1% by weight, more preferably no more than 0.6%. The gel according to the invention preferably has a calcium ion content of at least 0.05% by weight, more preferably at least 0.1%, further preferably in the range 0.10 to 0.45% or in the range 0.15 to 0.35%, by weight. The water content of the gel according to the invention is generally at least 85% by weight and may be at least 90%. The water content of the gel according to the invention is generally no more than about 97 or 98% by weight. The solids content (determined by oven drying) of the gel according to the invention is preferably in the range 3 to 10% by weight, more preferably in the range 3.5 to 8.0% by weight.

The alginate may be a high-G or high-M alginate. High-M alginate having an M:G ratio of more than about 50:50, more preferably in the range about 55:45 to about 75:25, may be preferred. It has surprisingly been found that fibrous gels are more readily formed by the method of the invention from high-M than from high-G alginates. The ratio by weight of calcium to sodium ions in a high-M alginate gel according to the invention is preferably no more than 50:50 and is preferably at least 5:95, more preferably at least 10:90. The ratio by weight of calcium to sodium ions in a high-G alginate gel according to the invention is preferably no more than 20:80 and is preferably at least 2:98. The ratio by weight of calcium to alginic acid in a high-M alginate gel according to the invention is preferably no more than 0.06:1 and is preferably at least 0.02:1. The ratio by weight of calcium to alginic acid in a high-G alginate gel according to the invention is preferably no more than 0.03:1 and is preferably at least 0.0025:1.

The alginate fiber used in the method of the invention generally has a unit weight in the range 1 to 10 decitex, preferably in the range 2 to 5 decitex. The alginate fiber may be used in the form of continuous filaments or staple fiber, although staple fiber is generally preferred. The staple length of such alginate fiber is not critical but may generally be in the range 5 to 100 mm. Fiber consisting of material of a range of decitex or staple length or both is suitable for use in the invention. Air-dry fiber or wet fiber, for example never-dried fiber, may be used in the invention. Before treatment with the solution of the solubilizing salt the alginate fiber may be mixed with other pharmaceutically acceptable fibers, for example pectin or carrageenin fibers. The alginate fiber is preferably provided in the form of a loose assembly of staple fiber, for example a carded web. Fabrics of alginate fiber, for example woven, knitted or non-woven fabrics, are generally less preferred. Treatment of alginate fiber with the solution of the solubilizing salt in the method of the invention swells the fiber. It has been found that fiber restrained by incorporation in a fabric generally does not swell during treatment with a solution of the solubilizing salt to the desired degree, and that in consequence a fibrous gel is not formed. Alginate powder does not form a fibrous gel when treated with an aqueous solution of a solubilizing salt.

The alginate fiber used in the method of the invention is conveniently a water-insoluble alginate, in particular calcium alginate. Other water-insoluble alginates, for example zinc alginate, may also be used. The cation in such water-insoluble alginates may be referred to as the insolubilizing cation. Water-insoluble alginate fiber containing more than one type of insolubilizing cation may also be used. Water-insoluble alginate fiber containing minor proportions of one or more solubilizing cations may be used. The water-insoluble alginate fiber may alternatively contain hydrogen cations, for example alginic acid fiber or calcium hydrogen alginate fiber. The insolubilising cation may comprise a polymeric cation, for example chitosan. Water-swellable alginate fiber, for example calcium sodium alginate fiber, may alternatively be used.

The solubilizing salt is preferably a sodium salt, for example sodium chloride. Other sodium salts having physiologically acceptable anions, for example sodium acetate and sodium citrate, may also be used but are generally less preferred. Solubilizing salts of other cations, for example magnesium, ammonium or substituted ammonium, may also be used. A solution of sodium alginate may be used. Mixtures of solubilizing salts may be used.

The concentration of solubilizing salt in the solution is preferably chosen so as to provide a gel containing a physiologically acceptable concentration of the solubilizing cation. Physiological or isotonic saline may be preferred as the solution for use in the method of the invention. The aqueous solution may optionally contain small proportions, generally no more than 10 per cent by weight, of one or more physiologically acceptable water-miscible organic solvents, for example ethanol.

The method of the invention may be carried out by submersing the alginate fiber in an excess of the solution, followed by filtration, for example under weak vacuum or gravity, to remove the excess liquor. For example, 1 part of fiber may be submersed in 20 to 100 parts of solution. The method of the invention is preferably carried out at or near ambient temperature. The gel forms rapidly on submersion, and filtration can generally be carried out shortly thereafter, for example within 1 to 10 minutes after submersion. The cycle of submersion and filtration may be repeated to provide a more hydrophilic product; for example the cycle may be carried out up to 10 or 15 times, often 3 to 6 times. Insolubilizing cation is progressively replaced by solubilizing cation during such repetitions of the cycle. The alginate material generally takes the form of a gelatinous fibrous mass after a single treatment and the form of a translucent or transparent fibrous gel according to the invention after several treatments. Filtration is generally continued after each submersion until the gelatinous fibrous mass appears visibly dry or until the fibrous gel stops dripping, as the case may be. The method of the invention may alternatively be carried out by repeatedly adding portions of the solution to alginate supported on a filter and allowing the solution to drain through the alginate. Alternatively, the method of the invention may be carried out by continuously passing the solution of the solubilizing salt through a thin bed of the alginate fiber until the fibrous gel is formed. Alternatively, the method of the invention may be performed by mixing suitably chosen alginate fiber with a suitable aqueous solution of a solubilizing salt so as to form a fibrous alginate gel directly without the need for any filtration step. This alternative method is generally less preferred, because it may be found to be difficult to apply sufficiently vigorous mixing to form a homogeneous gel while retaining the desired fibrous nature of the gel.

The alginate fiber should not be treated according to the method of the invention with the solution of solubilizing salt to such an extent that the resulting gel has essentially no fibrous structure. The alginate gel of the invention contains a sufficient minimum proportion of insolubilizing cation such that the gel possesses a fibrous structure as hereinbefore described.

The alginate gel of the invention may also be produced by treating water-soluble alginate fiber, for example sodium alginate fiber, with an aqueous solution of an insolubilizing salt, for example a calcium salt.

Alginate gel prepared according to the method of the invention can be dried to provide a material with a higher water absorbency, but it is generally preferred to use the gel as formed and collected.

The method of the invention may be carried out using sterile materials and under sterile conditions. Alginate fiber may be sterilized prior to treatment with the aqueous solution of the solubilising salt, for example by exposure to ionizing radiation, e.g. an electron beam or gamma rays, or to a chemical sterilizing agent, e.g. ethylene oxide. Fiber sterilized using gamma rays has been found to be liable to yield a lumpy gel which is prone to syneresis and this method of sterilization is therefore generally less preferred. Alginate gel according to the invention may be sterilized to ensure its sterility before or preferably after packaging, preferably by autoclaving, for example at 110°–130° C. for 10–30 minutes. Irradiation of the gel with gamma rays has generally been found to degrade the gel. The alginate gel of the invention may contain a free radical scavenger, for example a polyhydroxy alcohol such as mannitol or ribitol, to stabilize the gel against such effects of irradiation.

The alginate gel of the invention may contain a conventional preservative for medical alginates, for example propylene glycol. The alginate gel of the invention may contain medicaments such as pharmaceutical or antimicrobial agents. Such materials may be dissolved or suspended in the solution of the solubilizing salt so that they become incorporated into the gel during its manufacture.

The alginate gel of the invention is preferably packaged in a syringe, tube or sachet from which it can be extruded for application onto a wound on a human or animal body. The alginate gel may alternatively be packaged in other ways, for example in jars, trays or other containers or in the form of a slab or sheet, e.g. 1 to 10 mm thick, placed between protective polymer films. The alginate gel of the invention is preferably packaged in single dose form. The alginate gel of the invention is generally stable on storage in sterile form over at least several months, during which time the gel retains its fibrous nature and does not exhibit any significant degree of syneresis.

The alginate gels of the invention are moldable and highly conformable. They are deformable and may therefore be used as dressings on curved surfaces. They may be used to pack deep wounds. Stiffer gels may be preferred for direct application to a wound and less stiff gels for extrusion onto a wound. The gels of the invention are absorbent and transmit water vapour from the wound surface. They have a debriding effect on wounds and are non-dehydrating. Highly hypertonic gels may be indicated for use on chronic wounds in the inflammatory phase that are deep, discharging or infected. The gels of the invention may be removed from a wound when desired by washing with sterile distilled water or preferably with sterile saline solution.

The invention is illustrated by the following Examples.

EXAMPLE 1

A known weight of air-dry alginate fiber having known contents of solubilizing and insolubilizing cations (Na and Ca) and containing known proportions of mannuronic and guluronic acids (M:G ratio) was placed in a screw-top bottle. Aqueous sodium chloride solution (100 ml) was then added to the bottle. The top was fitted to the bottle, which was then shaken and allowed to stand for at least 2 minutes. The mixture consisting of swollen fiber or fibrous gel in saline solution was filtered under vacuum (approximately 34 kPa absolute) through a Whatman No. 1 filter paper on a Büchner funnel. The appearance of the collected fiber or gel was noted and its weight recorded. The ratio of the weight of liquor in the collected fiber or gel to the weight of the original alginate fiber was calculated (Gel Ratio). The volume of the filtrate was measured and its calcium content determined by titration against 0.1M EDTA. The amount of calcium in the collected fiber or gel was calculated by difference, and the amount of calcium associated with bone-dry (B.D.) alginate was calculated on the assumptions that the fiber or gel consisted of calcium sodium alginate in association with a liquor having the same composition as the filtrate and that no alginate was dissolved in the filtrate. The percentages by weight of alginic acid (AlgH), sodium, calcium and water and the calcium to sodium ratio by weight in the fiber or gel were also calculated. The steps of treatment with aqueous sodium chloride, filtration and analysis were repeated until the filtration step became excessively slow.

The following results were obtained using 2.5 g calcium alginate fiber having an M:G ratio 63:37 and 0.9% w/v saline solution:

TABLE 1

| Treatment No | Gel Ratio | Ca in B.D Alginate % | Appearance | AlgH % | Ca % | Na % | $H_2O$ % | Ca:Na |
| --- | --- | --- | --- | --- | --- | --- | --- | --- |
| 0 | — | 9.41 | F | 77.4 | 8.00 | 0.17 | 14.4 | 98:2 |
| 1 | 4.5 | 6.87 | G/F | 14.2 | 1.12 | 0.72 | 84.0 | 61:39 |
| 2 | 8.6 | 5.29 | F/G | 8.1 | 0.50 | 0.72 | 90.7 | 41:59 |
| 3 | 12.1 | 4.14 | F/G | 5.9 | 0.29 | 0.70 | 93.1 | 29:71 |
| 4 | 15.6 | 3.50 | F/G | 4.7 | 0.19 | 0.67 | 94.5 | 22:78 |
| 5 | 17.8 | 3.05 | F/G | 4.1 | 0.15 | 0.66 | 95.1 | 19:81 |
| 6 | 20.2 | 2.66 | F/G | 3.7 | 0.12 | 0.65 | 95.6 | 16:84 |
| 7 | 21.2 | 2.39 | F/G | 3.5 | 0.10 | 0.65 | 95.8 | 13:87 |

Appearance is recorded as F for dry fiber, as G/F for gelatinous fiber, and as F/G for fibrous gel.

EXAMPLE 2

Example 1 was repeated, except that the weight of calcium alginate fiber was 5.0 g. The following results were obtained:

TABLE 2

| Treatment No | Gel Ratio | Ca in B.D Alginate % | Appearance | AlgH % | Ca % | Na % | H₂O % | Ca:Na |
|---|---|---|---|---|---|---|---|---|
| 0 | — | 9.41 | F | 77.4 | 8.00 | 0.17 | 14.4 | 98;2 |
| 1 | 2.9 | 7.63 | G/F | 19.7 | 1.71 | 0.68 | 77.9 | 72:28 |
| 2 | 5.0 | 6.51 | G/F | 13.0 | 0.97 | 0.75 | 85.3 | 56:44 |
| 3 | 7.5 | 5.30 | F/G | 9.1 | 0.58 | 0.75 | 89.5 | 44:56 |
| 4 | 9.6 | 4.68 | F/G | 7.3 | 0.41 | 0.74 | 91.6 | 36:64 |
| 5 | 12 | 4.17 | F/G | 5.8 | 0.29 | 0.70 | 93.2 | 29:71 |
| 6 | 13.8 | 3.68 | F/G | 5.2 | 0.23 | 0.70 | 93.8 | 25:75 |
| 7 | 15.7 | 3.27 | F/G | 4.6 | 0.18 | 0.68 | 94.5 | 21:79 |
| 8 | 18.1 | 3.02 | F/G | 4.1 | 0.15 | 0.66 | 95.1 | 19:81 |
| 9 | 19.5 | 2.75 | F/G | 3.8 | 0.13 | 0.65 | 95.5 | 17:83 |

EXAMPLE 3

Example 1 was repeated, except that the weight of calcium alginate fiber was 1.25 g. The following results were obtained:

TABLE 3

| Treatment No | Gel Ratio | Ca in B.D Alginate % | Appearance | AlgH % | Ca % | Na % | H₂O % | Ca:Na |
|---|---|---|---|---|---|---|---|---|
| 0 | — | 9.41 | F | 77.4 | 8.00 | 0.17 | 14.4 | 98:2 |
| 1 | 7.1 | 5.78 | F/G | 9.5 | 0.64 | 0.75 | 89.1 | 46:54 |
| 2 | 12.8 | 3.81 | F/G | 5.6 | 0.26 | 0.73 | 93.4 | 26:74 |
| 3 | 17.6 | 2.84 | F/G | 4.2 | 0.14 | 0.69 | 95.0 | 17:83 |
| 4 | 19.4 | 2.24 | F/G | 3.8 | 0.10 | 0.69 | 95.4 | 13:87 |
| 5 | 23.5 | 1.77 | F/G | 3.2 | 0.07 | 0.65 | 96.1 | 10:90 |

It will be noted that the value of the Gel Ratio was essentially the same for a given calcium content in B.D. alginate in each of Examples 1–3.

EXAMPLE 4

Example 1 was repeated, except that 1.35% w/v saline solution was used. The following results were obtained:

TABLE 4

| Treatment No | Gel Ratio | Ca in B.D Alginate % | Appearance | AlgH % | Ca % | Na % | H₂O % | Ca:Na |
|---|---|---|---|---|---|---|---|---|
| 0 | — | 9.41 | F | 77.4 | 8.00 | 0.17 | 14.4 | 98:2 |
| 1 | 4.9 | 6.13 | G/F | 12.7 | 0.91 | 0.93 | 85.4 | 49:51 |
| 2 | 10.0 | 4.28 | F/G | 7.1 | 0.37 | 0.91 | 91.7 | 29:71 |
| 3 | 13.5 | 3.31 | F/G | 5.3 | 0.22 | 0.89 | 93.6 | 20:80 |
| 4 | 16.3 | 2.73 | F/G | 4.5 | 0.15 | 0.87 | 94.5 | 15:85 |
| 5 | 19.4 | 2.28 | F/G | 3.8 | 0.11 | 0.84 | 95.2 | 12:88 |

It will be noted that the value of the Gel Ratio was generally lower for a given calcium content in B.D. Alginate in Example 4 than in Examples 1–3.

EXAMPLE 5

Example 1 was repeated, except that a calcium sodium alginate fiber having an M:G ratio 25:75 was used. The following results were obtained:

TABLE 5

| Treatment No | Gel Ratio | Ca in B.D Alginate % | Appearance | AlgH % | Ca % | Na % | H₂O % | Ca:Na |
|---|---|---|---|---|---|---|---|---|
| 0 | — | 8.00 | F | 77.4 | 6.80 | 1.81 | 14.0 | 79:21 |
| 1 | 3.3 | 6.50 | G/F | 18.2 | 1.32 | 1.01 | 79.5 | 57:43 |
| 2 | 3.0 | 5.67 | G/F | 19.2 | 1.21 | 1.26 | 78.4 | 49:51 |
| 3 | 3.3 | 5.03 | G/F | 17.9 | 1.00 | 1.35 | 79.7 | 43:57 |
| 4 | 4.2 | 4.46 | G/F | 15.0 | 0.74 | 1.30 | 83.0 | 36:64 |
| 5 | 4.8 | 3.93 | G/F | 13.3 | 0.58 | 1.28 | 84.9 | 31:69 |
| 6 | 5.1 | 3.46 | G/F | 12.7 | 0.49 | 1.31 | 85.5 | 27:73 |
| 7 | 5.9 | 2.98 | G/F | 11.2 | 0.38 | 1.27 | 87.1 | 23:77 |
| 8 | 6.2 | 2.51 | F/G | 10.8 | 0.31 | 1.30 | 87.6 | 19:81 |
| 9 | 8.8 | 2.04 | F/G | 7.9 | 0.19 | 1.09 | 90.8 | 15:85 |
| 10 | 8.0 | 1.67 | F/G | 8.6 | 0.17 | 1.20 | 90.0 | 12:88 |
| 11 | 8.8 | 1.31 | F/G | 7.9 | 0.12 | 1.16 | 90.9 | 9:91 |
| 12 | 10.2 | 0.96 | F/G | 6.9 | 0.08 | 1.09 | 91.9 | 7:93 |
| 13 | 11.3 | 0.71 | F/G | 6.3 | 0.05 | 1.04 | 92.6 | 5:95 |
| 14 | 14.8 | 0.39 | F/G | 4.9 | 0.03 | 0.91 | 94.2 | 3:97 |

EXAMPLE 6

Example 1 was repeated with the following results:

| Treatment No | Gel Ratio | Appearance | AlgH % | Ca % | Na % | H₂O % | Ca:Na |
|---|---|---|---|---|---|---|---|
| 0 | — | F | 77.4 | 8.00 | 0.17 | 14.4 | 98:2 |
| 1 | 5.4 | G/F | 14.2 | 1.12 | 0.72 | 84.0 | 61:39 |
| 2 | 9.6 | F/G | 8.2 | 0.50 | 0.72 | 90.7 | 41:59 |
| 3 | 13.2 | F/G | 5.9 | 0.29 | 0.70 | 93.1 | 29:71 |
| 4 | 16.6 | F/G | 4.7 | 0.19 | 0.67 | 94.5 | 22:78 |
| 5 | 18.8 | F/G | 4.1 | 0.15 | 0.66 | 95.1 | 19:81 |
| 6 | 21.2 | F/G | 3.7 | 0.12 | 0.65 | 95.6 | 16:84 |

The amount of alginate in the filtrate from each treatment was assessed by precipitation with calcium chloride solution and gravimetric analysis. The composition of the collected fiber or gel was calculated taking this dissolved alginate into account, with the following results:

| Treatment No | AlgH % | Ca % | Na % | H₂O % | Ca:Na |
|---|---|---|---|---|---|
| 0 | 77.4 | 8.00 | 0.17 | 14.4 | 98:2 |
| 1 | 13.7 | 1.12 | 0.72 | 84.5 | 61:39 |
| 2 | 7.5 | 0.50 | 0.67 | 91.3 | 43:57 |
| 3 | 5.2 | 0.29 | 0.62 | 93.9 | 32:68 |
| 4 | 4.0 | 0.19 | 0.56 | 95.2 | 25:75 |
| 5 | 3.5 | 0.15 | 0.53 | 95.5 | 22:78 |
| 6 | 3.0 | 0.12 | 0.50 | 96.4 | 19:81 |

EXAMPLE 7

Calcium alginate fiber (25 g) having an M:G ratio 63:37 was submersed in 0.9% aqueous sodium chloride solution (1 l) and the resulting mixture poured through a 100-mesh nylon gauze and allowed to drain through it at atmospheric pressure. This process was carried out a total of three times. The alginate material on the gauze had the appearance of a fibrous gel. Weak vacuum was then applied until the gel stopped dripping. The gel weighed 283 g, contained 0.32% by weight calcium and had a solids content (measured by oven-drying) of 6.4% by weight. The alginate content (expressed as alginic acid) of the gel was estimated to be about 6.5% by weight.

EXAMPLE 8

Calcium alginate fiber (2.5 g) having an M:G ratio 63:37 was added to a solution of trisodium citrate (0.5 g) in water (50 ml) with vigorous mixing. A fibrous gel formed immediately. The fibrous gel was calculated to contain 0.44% by weight calcium and to have a solids content of 5.5% by weight. If mixing was insufficiently vigorous, the gel tended to be lumpy; if mixing was excessively vigorous, the gel tended to lose its fibrous character. The alginate content (expressed as alginic acid) of the gel was estimated to be about 4% by weight.

EXAMPLE 9

Calcium alginate fiber (2.5 g) having an M:G ratio 63:37 was added with vigorous stirring to an aqueous solution containing 2.5% w/w sodium alginate (100 g). A fibrous gel formed immediately. The gel was calculated to contain 0.23% by weight calcium and to have a solids content of 5.0% by weight. If mixing was insufficiently vigorous, the gel tended to be lumpy; if mixing was excessively vigorous, the gel tended to lose its fibrous character. The alginate content (expressed as alginic acid) of the gel was estimated to be about 4% by weight.

EXAMPLE 10

Calcium alginate fiber (5 g) having an M:G ratio 63:37 was washed with a solution which was a mixture of 0.1M HCl (200 ml) with water (50 ml). Excess liquor was drained off, and its calcium content assayed by titration against EDTA. This showed that 66% of the calcium ions had been removed from the fiber and replaced by hydrogen ions. The fiber was washed with distilled water and the wet fiber added to 0.2M NaOH (70 ml) with vigorous stirring to form a fibrous alginate gel. The calcium content of the gel was estimated to be about 0.41% and the solids content to be about 6.7% by weight. The alginate content (expressed as alginic acid) of the gel was estimated to be about 5.5% by weight.

EXAMPLE 11

Calcium alginate fiber (2.5 g) having an M:G ratio 63:37 was added with stirring to a 9.0% w/v aqueous solution of sodium chloride (250 ml). Excess liquor was removed by filtration under weak vacuum. The fibrous gel so collected weighed 24.2 g, was calculated to have calcium content 0.23% by weight, solids content 14.8% by weight and sodium chloride content about 9% by weight. The alginate content (expressed as alginic acid) of the gel was estimated to be about 7.5% by weight.

EXAMPLE 12

Absorption capacity of alginate gels was assessed in the following manner. A known quantity of the gel (10 +/− 0.5 g) was placed in a No. 1 sintered glass crucible and lightly pressed down. A solution containing 142 mM sodium and 2.5 mM calcium (made by dissolving the appropriate amounts of the chlorides in water) was added in 0.5 ml aliquots to the gel at 5-minute intervals until liquid was seen to pass through the gel and drip from the stem of the crucible. The total amount of solution added was recorded.

Fibrous alginate gels according to the invention were prepared by the method of Example 1, except that 25 g calcium alginate fiber having an M:G ratio 63:37 was used. The following results were obtained, in which 'gel weight' is the weight of the fibrous gel obtained after treating the fiber repeatedly with portions of sodium chloride solution and filtration:

| Gel Weight g | Ca % w/w | Solids % w/w | Absorption Capacity g |
|---|---|---|---|
| 302 | 0.35 | 7.7 | 7.5 |
| 334 | 0.27 | 6.1 | 6.5 |
| 369 | 0.20 | 5.2 | 6.0 |
| 399 | 0.15 | 4.6 | 6.0 |
| 437 | 0.13 | 4.1 | 6.0 |

EXAMPLE 13

Stiffness of alginate gels was measured in the following manner. A plastic sample container 60 mm in diameter and 50 mm deep was filled with the gel to be tested. The container was placed on the platform of a Stevens LFRA Texture Analyser fitted with a cylindrical probe of 1 in. (25 mm) diameter and 1.5 in. (38 mm) long. The probe was driven into the gel at 2 mm/sec to a depth of 10 mm and the result recorded in grams. The following results were obtained on gels prepared as described in Example 12:

| Gel Weight g | Stiffness g |
|---|---|
| 288 | 791 |
| 302 | 675 |
| 312 | 594 |
| 344 | 446 |
| 388 | 326 |
| 426 | 219 |
| 462 | 164 |

Stiffer gels of the above type are considered to be more suitable for application to accessible wounds where the gel can be molded to fit the wound. Less stiff gels of the above type are considered to be more suitable for application by syringe to inaccessible wounds.

EXAMPLE 14

Fibrous alginates prepared as described in Example 12 were sterilized by autoclaving at 121° C. for 15 minutes. Absorption capacity measured by the method of Example 12 was reduced by 0.5 ml at all gel weights compared with the unsterilized gel. The following results were obtained for stiffness, using the method of Example 13 and expressed in grams, before and after autoclaving:

| Before | After |
|---|---|
| 934 | 461 |
| 617 | 335 |
| 446 | 223 |
| 409 | 196 |
| 327 | 151 |
| 244 | 88 |
| 164 | 66 |

COMPARATIVE EXAMPLE 1

A known weight of a needle-punched nonwoven calcium sodium alginate fiber wound dressing (M:G ratio 25:75, Ca:Na ratio 80:20), available from Britcair Limited under the Trademark "Kaltostat", was thoroughly wetted with water or 0.9% w/v saline solution and reweighed. In each case the wetted dressing took the form of a translucent coherent fabric sheet with high structural integrity which offered resistance to being torn by hand. The wetted dressings were not pasty or gelatinous and could not be molded, spread or extruded. The wetted dressings were calculated to have the following compositions:

| Treatment | Weight Ratio | AlgH % | Ca % | Na % | $H_2O$ % | Ca:Na |
|---|---|---|---|---|---|---|
| Water | 13.8 | 5.7 | 0.50 | 0.12 | 92.7 | 80:20 |
| Water | 13.0 | 6.0 | 0.53 | 0.13 | 92.3 | 80:20 |
| Saline | 11.2 | 7.0 | 0.61 | 0.48 | 91.0 | 56:44 |
| Saline | 10.3 | 7.6 | 0.66 | 0.49 | 90.3 | 58:42 |

What is claimed is:

1. An alginate gel in the form of a moldable water-soluble fibrous paste, having an alginate content expressed as alginic acid in the range of 2 to 11 percent by weight, said alginate containing mannuronic and guluronic acid units in a mannuronic acid:guluronic acid ratio in the range of about 55:45 to about 75:25, said paste produced by the process comprising treating water insoluble or water swellable alginate fiber with an aqueous solution of a solubilizing salt.

2. An alginate gel according to claim 1, wherein said alginate content is in the range 3 to 7 percent by weight.

3. An alginate gel according to claim 1, which contains sodium ions in an amount in the range 0.6 to 1.4 percent by weight.

4. An alginate gel according to claim 1, which contains sodium ions in an amount in the range 0.65 to 0.75 percent by weight.

5. An alginate gel according to claim 1, which contains calcium ions in an amount in the range 0.05 to 0.60 percent by weight.

6. An alginate gel according to claim 1, which contains calcium ions in an amount in the range 0.10 to 0.45 percent by weight.

7. An alginate gel according to claim 1, which has a solids content (determined by oven drying) in the range 3 to 10 percent by weight.

8. An alginate gel according to claim 1, which has a solids content (determined by oven drying) in the range 3.5 to 8.0 percent by weight.

9. The alginate gel according to claim 1 wherein the alginate fiber is provided for treatment in the form of a loose assembly of staple fiber.

10. The alginate gel according to claim 1 wherein the alginate fiber is calcium alginate fiber.

11. The alginate gel according to claim 1, wherein the solubilizing salt is sodium chloride.

12. The alginate gel according to claim 1, wherein the aqueous solution of a solubilizing salt is physiological or isotonic saline.

* * * * *